United States Patent
Preiss et al.

(10) Patent No.: US 7,855,723 B2
(45) Date of Patent: Dec. 21, 2010

(54) IMAGE REGISTRATION USING LOCALLY-WEIGHTED FITTING

(75) Inventors: Assaf Preiss, Shimshit (IL); Roy Tal, Haifa (IL); Ziv Kitlaro, M.P. Menashe (IL); Zafrir Patt, Ramat-Hasharon (IL)

(73) Assignee: Biosense Webster, Inc., Diamond Bar, CA (US)

( * ) Notice: Subject to any disclaimer, the term of this patent is extended or adjusted under 35 U.S.C. 154(b) by 1005 days.

(21) Appl. No.: 11/385,060

(22) Filed: Mar. 21, 2006

(65) Prior Publication Data

US 2007/0223794 A1  Sep. 27, 2007

(51) Int. Cl.
G06T 15/00 (2006.01)
G06K 9/00 (2006.01)
G06K 7/00 (2006.01)
G06K 9/20 (2006.01)

(52) U.S. Cl. .......... 345/419; 382/128; 382/312
(58) Field of Classification Search ........ 382/128, 382/293, 294, 312; 345/419
See application file for complete search history.

(56) References Cited

U.S. PATENT DOCUMENTS

| | | | |
|---|---|---|---|
| 5,391,199 A | 2/1995 | Ben-Haim | |
| 5,443,489 A | 8/1995 | Ben-Haim | |
| 5,568,384 A | 10/1996 | Robb et al. | |
| 5,944,022 A | 8/1999 | Nardella et al. | |
| 5,983,126 A | 11/1999 | Wittkampf | |
| 6,239,724 B1 | 5/2001 | Doron et al. | |
| 6,332,089 B1 | 12/2001 | Acker et al. | |
| 6,456,864 B1 | 9/2002 | Swanson et al. | |
| 6,456,867 B2 * | 9/2002 | Reisfeld | 600/407 |
| 6,560,354 B1 * | 5/2003 | Maurer et al. | 382/131 |
| 6,618,612 B1 | 9/2003 | Acker et al. | |
| 6,690,963 B2 | 2/2004 | Ben-Haim et al. | |
| 7,672,705 B2 * | 3/2010 | Lachaine et al. | 600/407 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2005/0094898 A1 * | 5/2005 | Xu et al. | 382/294 |

FOREIGN PATENT DOCUMENTS

WO  WO 96/05768 A1  2/1996

OTHER PUBLICATIONS

U.S. Appl. No. 11/030,934—pending, Biosense Webster, Inc.

* cited by examiner

*Primary Examiner*—Kee M Tung
*Assistant Examiner*—Jacinta Crawford
(74) *Attorney, Agent, or Firm*—Louis J. Capezzuto (57) ABSTRACT

A computer-implemented method for image registration includes accepting a three-dimensional (3-D) image of an organ. The image includes a first plurality of image points with respective image coordinates. A map defining a distribution of values of a physiological parameter over the organ is accepted. The map includes a second plurality of map points with respective map coordinates. Confidence levels are associated with one or more of the map coordinates and image coordinates. Weights are assigned to at least some of the map points and image points responsively to the confidence levels of the respective map coordinates and image coordinates. The 3-D image is fitted with the map by calculating a geometrical transformation between the map coordinates and the image coordinates based on the weights.

26 Claims, 4 Drawing Sheets

IMAGE REGISTRATION USING LOCALLY-WEIGHTED FITTING

FIELD OF THE INVENTION

The present invention relates generally to medical imaging and mapping, and particularly to methods and systems for registering maps of physiological parameters with three-dimensional (3-D) images.

BACKGROUND OF THE INVENTION

In various medical applications, a computer-generated reconstruction of body parts or organs is displayed to a user. For example, U.S. Pat. No. 6,456,867, whose disclosure is incorporated herein by reference, describes a method of reconstructing a map of a volume. The method includes determining coordinates of locations on a surface of the volume, and generating a grid of points defining a reconstruction surface in 3-D space in proximity to the determined locations. For each of the points on the grid, a respective vector is defined dependent on a displacement between one or more of the points on the grid and one or more of the locations. The reconstruction surface is then adjusted by moving substantially each of the points on the grid responsive to the respective vector, so that the reconstruction surface is deformed to resemble the configuration of the surface.

In some applications, images from multiple modalities, or imaging sources, are fitted with one another and presented. For example, U.S. Pat. No. 5,568,384, whose disclosure is incorporated herein by reference, describes a method for synthesizing 3-D multimodality image sets into a single composite image. Surfaces are initially extracted from two or more different images to be matched using semi-automatic segmentation techniques. The surfaces are represented as contours with common features to be matched. A distance transformation is performed for one surface image, and a cost function for the matching process is developed using the distance image. The geometric transformation includes three-dimensional translation, rotation and scaling to accommodate images of different position, orientation and size. The matching process involves searching the multi-parameter space and adjusting a surface or surfaces to find the best fit among them, which minimizes the cost function.

SUMMARY OF THE INVENTION

Some medical methods and systems measure and present a map showing the distribution of a certain physiological parameter across an imaged organ. For example, an electro-anatomical map showing the distribution of local electrical potentials across the endocardium (the inner surface of the heart) is useful in various cardiological procedures.

It is sometimes desirable to display the parameter map together with a 3-D image of the organ, such as a Magnetic Resonance Imaging (MRI), Computerized Tomography (CT), X-ray or ultrasound-based image. In order to jointly display the map and 3-D image, the two views of the organ should first be registered to a common coordinate system. In some cases, the coordinates of the parameter map and/or the 3-D image may have varying confidence levels. Points or areas of the map or image having low confidence levels may have an adverse effect on the accuracy of the registration process.

In order to improve the accuracy of the registration process, embodiments of the present invention provide methods and systems for registering a parameter map with a 3-D image while taking into account the varying confidence levels of the map coordinates and/or image coordinates. The 3-D image typically comprises a plurality of image points with respective image coordinates. In some embodiments, the image points define a 3-D solid volume model, surface model or 3-D wire-frame model of the imaged organ or parts thereof. In some embodiments, weights are assigned to the map points and image points responsively to confidence levels of the map and image coordinates. The map and the 3-D image are then fitted together by calculating and applying a geometrical transformation based on the weights.

In some exemplary embodiments described herein, the parameter map is obtained using a magnetic position tracking system. In these embodiments, a probe, such as a catheter, is fitted with a sensor, such as an electrode, which measures the physiological parameter at different locations in the imaged organ. The position tracking system is used to track the coordinates of the probe when making the measurements, so as to produce a map indicating a distribution of the parameter values across the organ.

There is therefore provided, in accordance with an embodiment of the present invention, a computer-implemented method for image registration, including:

accepting a three-dimensional (3-D) image of an organ, the image including a first plurality of image points with respective image coordinates;

accepting a map defining a distribution of values of a physiological parameter over the organ, the map including a second plurality of map points with respective map coordinates;

associating respective confidence levels with one or more of the map coordinates and image coordinates;

assigning weights to at least some of the map points and image points responsively to the confidence levels of the respective map coordinates and image coordinates; and fitting the 3-D image with the map by calculating a geometrical transformation between the map coordinates and the image coordinates based on the weights.

In an embodiment, accepting the map includes measuring the values of the physiological parameter at the respective map coordinates using a position tracking system. Measuring the values and the map coordinates may include moving a probe including a position sensor and a sensor measuring the physiological parameter over multiple locations in the organ, and performing respective multiple measurements of the physiological parameter and of a position of the position sensor at the locations.

In another embodiment, the method includes superimposing the values of the physiological parameter onto the 3-D image using the geometrical transformation, and displaying the superimposed values and 3-D image to a user.

In yet another embodiment, fitting the 3-D image with the map includes defining distances between at least some of the image points and respective map points, applying the weights assigned to the respective map points and image points to the distances to produce weighted distances, and calculating a cumulative weighted distance metric based on the distances, the metric indicative of an accuracy of the geometrical transformation in fitting the 3-D image with the map.

In still another embodiment, applying the weights includes multiplying a square of the distances by the respective weights to produce the weighted distances, and calculating the cumulative weighted distance metric includes summing the weighted distances.

In an embodiment, fitting the 3-D image with the map further includes modifying the geometrical transformation so as to minimize the cumulative weighted distance metric.

In another embodiment, fitting the 3-D image with the map includes identifying an anatomical landmark external to the organ that appears in the 3-D image, acquiring a respective map point at a location of the anatomical landmark, and registering an image coordinate of the anatomical landmark in the 3-D image with a map coordinate of the acquired map point.

In yet another embodiment, associating the confidence levels includes accepting the confidence levels from a user. Additionally or alternatively, associating the confidence levels includes automatically determining the confidence levels based on the map points and image points. Automatically determining the confidence levels may include detecting a distortion in at least one of the map coordinates and image coordinates and assigning the confidence levels responsively to a level of the distortion. Additionally or alternatively, automatically determining the confidence levels includes assigning the confidence levels responsively to at least one of:

a density of the respective one or more of the map coordinates in the map;

an electrical tissue characteristic in a vicinity of the respective map coordinates and image coordinates;

a physiological tissue characteristic in the vicinity of the respective map coordinates and image coordinates;

a distance of the respective map coordinates and image coordinates from a registration landmark identified in both the map and the 3-D image; and a physiological characteristic of the registration landmark.

In an embodiment, accepting the 3-D image includes accepting at least one of a solid model, a surface model and a wire-frame model of the organ defined by at least some of the image points.

There is additionally provided, in accordance with an embodiment of the present invention, apparatus for image registration, including:

an interface, which is arranged to accept a three-dimensional (3-D) image of an organ, the image including a first plurality of image points with respective image coordinates, and to further accept a map defining a distribution of values of a physiological parameter over the organ, the map including a second plurality of map points with respective map coordinates; and a processor, which is arranged to associate respective confidence levels with one or more of the map coordinates and image coordinates, to assign weights to at least some of the map points and image points responsively to the confidence levels of the respective map coordinates and image coordinates, and to fit the 3-D image with the map by calculating a geometrical transformation between the map coordinates and the image coordinates based on the weights.

There is also provided, in accordance with an embodiment of the present invention, a computer software product for image registration, the product including a computer-readable medium in which instructions are stored, which instructions, when read by a computer, cause the computer to accept a pre-acquired three-dimensional (3-D) image of an organ, the image including a first plurality of image points with respective image coordinates, to accept a map defining a distribution of values of a physiological parameter over the organ, the map including a second plurality of map points with respective map coordinates, to associate respective confidence levels with one or more of the map coordinates and image coordinates, to assign weights to the map points and image points responsively to the confidence levels of the respective map coordinates and image coordinates, and to fit the 3-D image with the map by calculating a geometrical transformation between the map coordinates and the image coordinates based on the weights.

The present invention will be more fully understood from the following detailed description of the embodiments thereof, taken together with the drawings in which:

DETAILED DESCRIPTION OF EMBODIMENTS

System Description

Figure 1A:
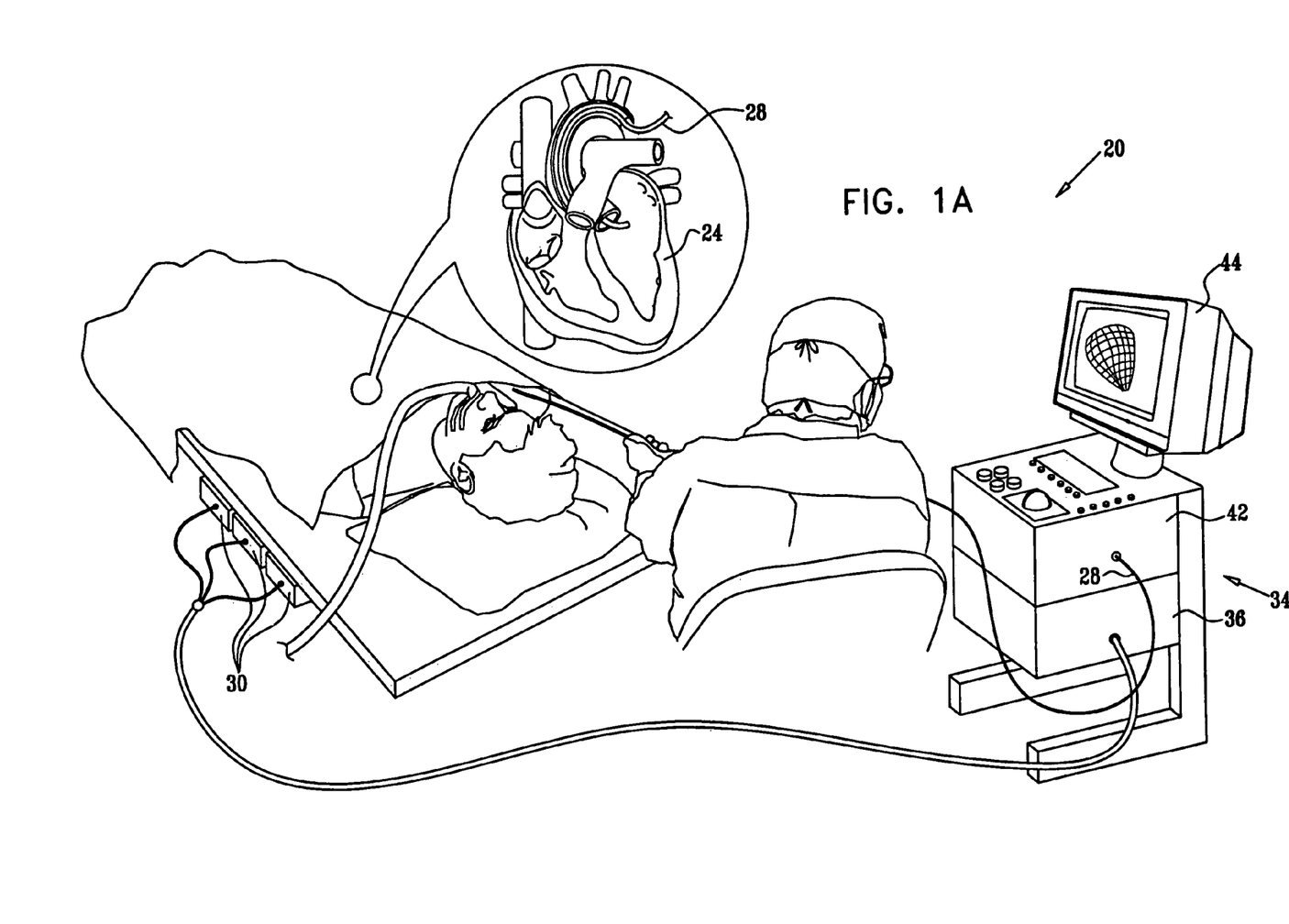
FIG. 1A is a schematic, pictorial illustration of a system for magnetic position tracking, in accordance with an embodiment of the present invention.

FIG. 1A is a schematic, pictorial illustration of a magnetic position tracking system 20 for imaging and mapping a heart 24 of a patient, in accordance with an embodiment of the present invention. The system of FIG. 1A serves to demonstrate an exemplary system, which can be used to obtain and present parameter maps. Although the embodiments described herein mainly refer to electro-anatomical maps obtained using a magnetic position tracking system, parameter maps can be obtained using any other means known in the art, such as using ultrasonic or impedance-based tracking systems. Exemplary impedance-based tracking systems are described in U.S. Pat. Nos. 5,983,126, 6,456,864, and 5,944,022, and in U.S. patent application Ser. No. 11/030,934, filed Jan. 7, 2005, whose disclosures are incorporated herein by reference.

In system 20, a catheter 28 is inserted by a physician into a chamber of heart 24 through a vein or artery. System 20 determines and displays the position and orientation coordinates of catheter 28. Although the embodiments described hereinbelow mainly refer to imaging of the heart, the methods and systems described herein can be used to image any suitable organ. Thus, in the context of the present invention and in the claims, the term "organ" is used to describe any imaged body part or tissue, which may comprise entire organs or parts thereof.

System 20 comprises field generators, such as field generating coils 30, which are located in fixed, known positions external to the patient. Coils 30 generate magnetic fields in a predefined working volume around heart 24. A position sensor fitted in the distal end of catheter 28 senses the magnetic fields in its vicinity.

The position sensor produces and transmits, in response to the sensed fields, position signals to a console 34. The console comprises a tracking processor 36 that calculates the location and orientation of catheter 28 with respect to coils 30, based on the position signals sent by the position sensor. The location and orientation coordinates of catheter 28 are displayed to the physician using a display 44.

System 20 comprises a display processor 42, which accepts the information measured by the position tracking system, as well as externally-supplied pre-acquired 3-D images. Display processor 42 registers the parameter map with the pre-acquired 3-D image, and presents the registered map and image to the physician, as will be explained below.

Figure 1B:
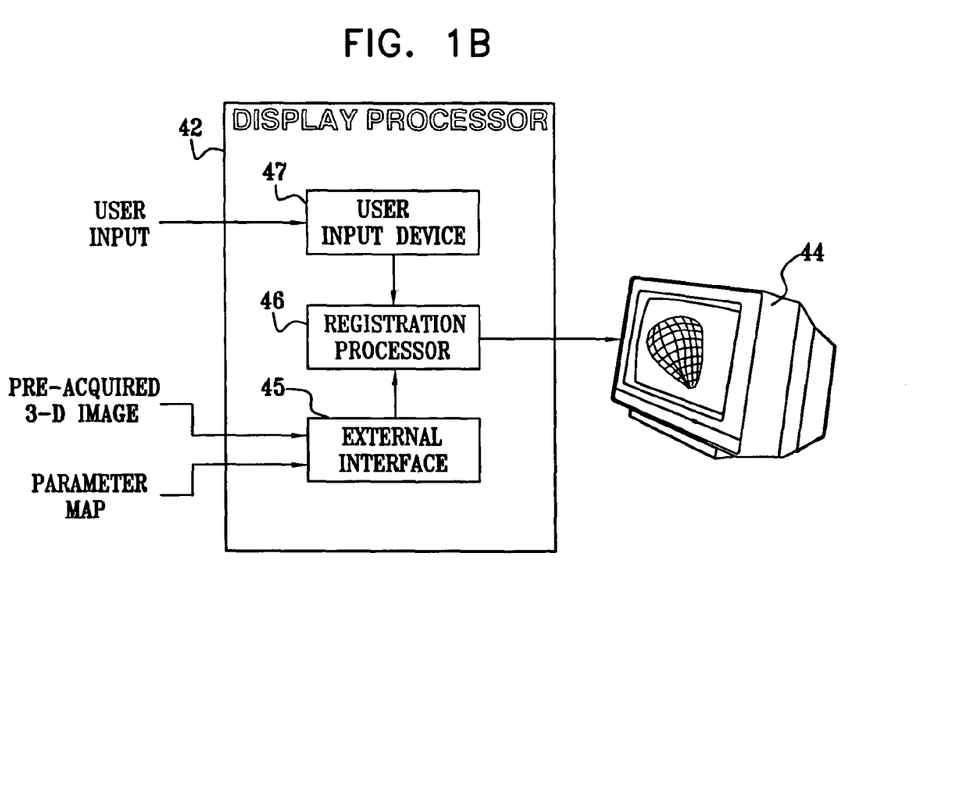
FIG. 1B is a block diagram that schematically illustrates a display processor, in accordance with an embodiment of the present invention.

FIG. 1B is a block diagram that schematically illustrates details of display processor 42, in accordance with an embodiment of the present invention. Processor 42 comprises an external interface 45, which accepts the pre-acquired 3-D image and parameter map. Processor 42 also comprises a registration processor 46, which performs the registration methods described herein and outputs the registered 3-D image and parameter map to display 44. Processor 42 interacts with a user, such as a physician, using a user input device 47, such as a keyboard, mouse or trackball. As noted above, display processor 42 can accept 3-D images and parameter maps from any suitable system or source.

Typically, tracking processor 36 and display processor 42 comprise general-purpose computers, which are programmed in software to carry out the functions described herein. The software may be downloaded to the processors in electronic form, over a network, for example, or it may alternatively be supplied to the processors on tangible media, such as CD-ROM. Processors 36 and 42 may be standalone units. Alternatively, the functions of processors 36 and 42 may be combined with one another or integrated with other elements of system 20.

Figure 2:
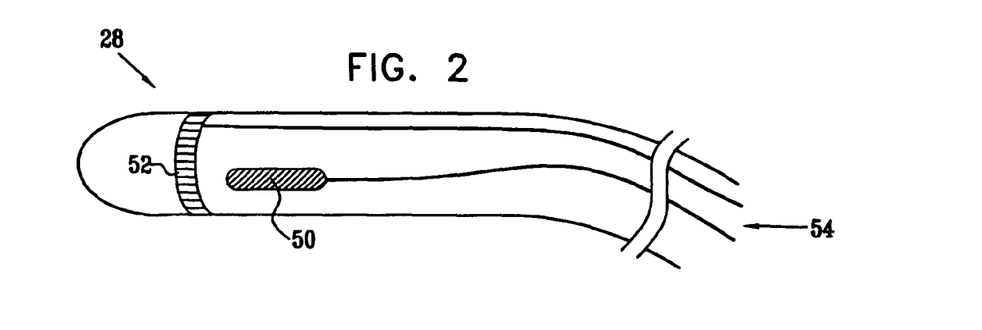
FIG. 2 is a schematic, pictorial illustration of a catheter, in accordance with an embodiment of the present invention.

FIG. 2 is a schematic, pictorial illustration of the distal end of catheter 28, in accordance with an embodiment of the present invention. Catheter 28 comprises a position sensor 50, which senses the magnetic fields generated by coils 30. In addition, catheter 28 comprises an electrode 52, which senses a physiological parameter in its vicinity.

For example, in some embodiments electrode 52 senses the local electrical potential in its vicinity. In these embodiments, the distal end of catheter 28 is brought in close proximity to various points on the endocardium (the inner surface of the heart). Electrode 52 is then used to sense the local electrical potentials on the endocardial surface. In alternative embodiments, catheter 28 may comprise one or more electrodes 52 for sensing any other suitable physiological parameters, such as temperature and pressure. In some embodiments, the catheter may be fitted with a chemical sensor for sensing a particular chemical composition in its vicinity.

Position sensor 50 and electrode 52 are connected to console 34 using suitable cables 54 running through catheter 28, or using a wireless connection (not shown). Tracking processor 36 associates the measured location coordinates of catheter 28 with the parameter measured by electrode 52. Thus, by moving the catheter through a plurality of locations in the heart, the physician is able to obtain a three-dimensional map of the parameter.

In the exemplary configuration of FIGS. 1A and 2, for example, system 20 obtains and displays an electro-anatomical map showing the distribution of local electrical potentials across the endocardiac surface. Such electro-anatomical mapping can be used for detecting and/or predicting various heart disorders and for planning related medical procedures, such as ablation. In alternative embodiments, other types of electrodes and sensors can be used to obtain maps of other parameters of interest. Typically, the parameter map comprises a plurality of map points. Each map point comprises a particular value of the parameter and is associated with a respective map coordinate.

The system configuration of FIGS. 1A and 2 is an exemplary configuration chosen for the sake of conceptual clarity. The methods described herein can be used in conjunction with any other suitable position tracking system or method. Some systems and methods for magnetic position tracking are described, for example, in PCT Patent Publication WO 96/05768, U.S. Pat. Nos. 5,391,199, 5,443,489, 6,690,963, 6,239,724, 6,618,612 and 6,332,089, and U.S. Patent Application Publications 2002/0065455 A1, 2003/0120150 A1 and 2004/0068178 A1, whose disclosures are all incorporated herein by reference. As noted above, parameter maps may alternatively be produced using any other suitable method or system.

Registration of Parameter Maps with Images

In some practical cases, it is desirable to display the parameter map projected onto a 3-D image of the mapped organ. In most cases, the 3-D image is acquired in advance, prior to the mapping procedure, and is thus referred to as a "pre-acquired" image. Alternatively, the 3-D image may be acquired concurrently with the mapping process or afterwards. In any case, dual-modality display, combining map and image information, generally improves the physician's understanding of the parameter map. For example, features of interest in the imaged organ can be easier to locate and examine using such common display.

The 3-D image may originate from a Magnetic Resonance Imaging (MRI) system, a Computerized Tomography (CT) system, an X-ray imaging system, an ultrasonic imaging system or any other suitable imaging system or source. Since the map and the 3-D image originate from different systems generally having different coordinate systems, the two views of the imaged organ should be registered, or fitted with one another, before they are displayed.

Typically, the 3-D image is represented and provided to display processor 42 as a plurality of image points. Each image point comprises a value (e.g., grey level or color) and is associated with a respective image coordinate. In some cases, the imaged organ or parts thereof may be represented in the 3-D image as a solid volume model, surface model or wire-frame model defined by at least part of the image points. In the context of the present patent application and in the claims, the term "image points" is used to describe any suitable representation of the 3-D image, such as various volumetric, surface and wire-frame representations defined by the image points. The registration methods described herein can be used to register parameter maps with 3-D images having any such representation. The 3-D image is typically provided to display processor 42 as a data file and may be provided using any convenient digital means, such as a network connection or a magnetic storage device, or using analog means such as a frame grabber.

The process of registering the parameter map with the 3-D image can be formulated as a task of finding a geometrical transformation that best fits the map with the 3-D image. Such a geometrical transformation may comprise translation, rotation and/or scaling of the image coordinates, so as to best fit the map. Alternatively, the geometrical transformation can be equivalently defined as fitting the parameter map onto the 3-D image, or transforming both map and image to an arbitrary reference coordinate system. The methods described below can be used to determine any such geometrical transformation.

In some embodiments, one of the two modalities used comprises a real-time modality, whereas the other modality comprises a non-real-time modality. For example, a parameter map measured in real-time by a position tracking system can be registered with a pre-acquired MRI or CT image. In such embodiments, it is often preferable, although not mandatory, to define the geometrical transformation as translating the coordinate system of the non-real-time modality to the coordinate system of the real-time modality.

The quality of the registration process is often evaluated by a cumulative distance metric that quantifies the distance between the map and the 3-D image. For example, in some embodiments, each map point denoted $M_i$ is associated with a corresponding image point denoted $I_i$. The distance between map point $M_i$ and its corresponding image point $I_i$ is denoted $d_i$. Distance $d_i$ typically denotes a three-dimensional Euclidean distance calculated between the coordinates of the map point and image point. An exemplary cumulative distance metric is given by $$D = \sqrt{\sum_i d_i^2} \qquad [1]$$

wherein i sums over the pairs of corresponding map points and image points. The registration of the map with the 3-D image thus comprises determining a geometrical transformation that minimizes the cumulative distance metric D.

In some cases, however, the coordinates of the map points and/or image points have varying confidence levels regarding the accuracy of the location of the point in question. For example, some areas of the parameter map may have a high density of map points, resulting in a higher confidence level. Other areas of the map may have fewer map points, often causing a lower confidence level.

Confidence levels can also be assigned in response to a distortion detected in the map or in the 3-D image (e.g., in specific image points or in areas of the solid, surface or wire-frame representation of the 3-D image). For example, areas of the map exhibiting high variance of the coordinate values may be assumed to contain a higher level of measurement noise, and consequently have a lower confidence level in comparison with smoothly-varying areas. Additionally or alternatively, an area of the imaged organ known to be characterized by high temporal variations (i.e., an area whose shape changes significantly and/or rapidly over time) can also be considered to have a lower confidence level.

The distortion in the map may also comprise a deformation in the geometrical shape of an area of the map, in comparison with the corresponding area in the 3-D image. Some exemplary methods, which can be used for determining areas of low confidence level in a measured map are also described in U.S. Pat. No. 6,456,867, cited above. Additionally or alternatively, the assignment of confidence levels to map points can be based on any other suitable criterion or combination of criteria.

Image points or areas of the 3-D image may also have varying confidence levels related to their location accuracy. For example, areas of the 3-D image may have a wrong segmentation (e.g., an area of the organ missing from the image or remains of other organs or organ parts combined with the target organ). Some areas of the 3-D image may have lower spatial or temporal resolution.

Map points and/or image points having low confidence levels can introduce errors into the geometrical transformation, resulting in a non-optimal registration. Therefore, it can be appreciated that taking the confidence levels into account when evaluating the geometrical transformation can significantly improve the quality of the registration. Areas of low confidence level can be prevented from distorting the transformation, and areas of higher confidence can be emphasized.

In order to reduce the effect of map and image points having low confidence levels, the methods described herein assign weights to the map and/or image points responsively to their confidence levels. The weights are then applied to the distances summed to provide the cumulative distance metric. The resulting metric is referred to as a weighted cumulative distance metric. Typically, the weights are proportional to the confidence levels so that map and image points having low confidence levels are assigned lower weights, and vice versa.

For example, in some embodiments, each map point $M_i$ is assigned a weight denoted $w_i$ based on the confidence level of the map point. In these embodiments, an exemplary weighted cumulative distance metric is given by $$D = \sqrt{\sum_i w_i d_i^2} \qquad [2]$$

Alternatively, other suitable cumulative distance metrics based on weights applied to the distances can also be used. Determining a geometrical transformation that minimizes the weighted cumulative distance metric provides a high accuracy registration of the parameter map with the pre-acquired 3-D image, taking into account the varying confidence levels of the map and image points.

In some embodiments, the registration process can utilize anatomical landmarks located outside the organ. In these embodiments, the physician identifies one or more anatomical features outside the organ that appear in the 3-D image, to be used as registration landmarks, or anchors. For example, when mapping the heart, the physician may choose a point or points on the aorta, such as the bifurcations of the major vessels from the aortic arch. As another example, the physician may choose the ostium of the inferior or superior vena cava. The physician then maneuvers catheter 28 so that its tip contacts the feature in question, and indicates the corresponding location on the pre-acquired 3D image on display 44.

By registering the landmark, the physician effectively identifies a map point and a corresponding image point that are known to match one another. When using the aorta or vena cava as landmarks, the physician may register the landmark while inserting the catheter through the blood vessel into the heart. As a result, the electro-anatomical map is already pre-registered with the pre-acquired 3-D image when catheter 28 enters the heart to begin the mapping procedure.

Weights can be assigned either automatically by the system or manually by the user. In some embodiments, manual weight assignment can be performed at any time during the procedure. Automatic weight assignment may depend on the tissue properties in the relevant area. When external landmarks are used, the weight assignment may depend on the distance of the landmark from the map or image point in question. For example, a landmark in the inferior vena cava can be automatically assigned a lower weight due to its soft and floppy nature and its distance from the left atrium.

Figure 3A:
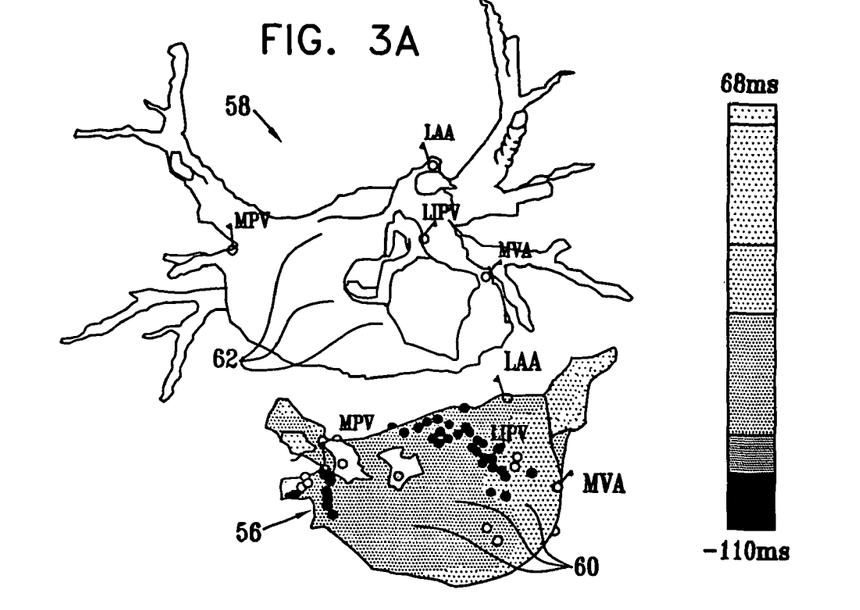
FIGS. 3A and 3B are diagrams that schematically illustrate an electro-anatomical map projected onto a three-dimensional (3-D) image of a heart, in accordance with an embodiment of the present invention.
Figure 3B:
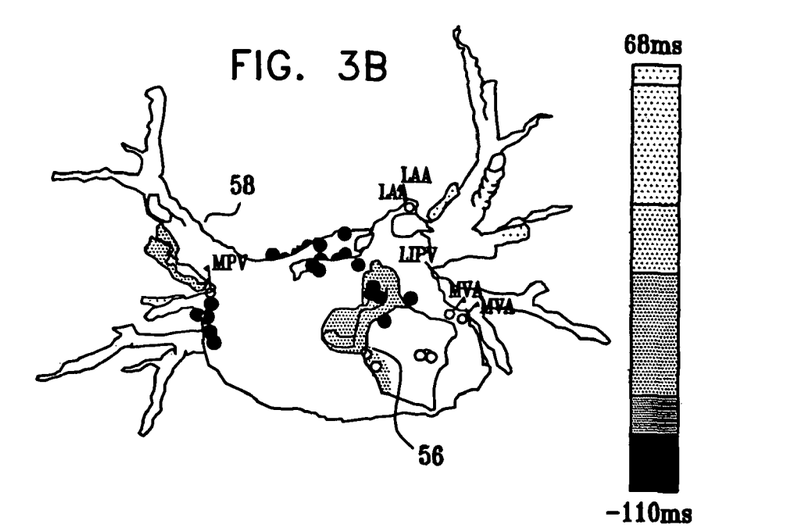

FIGS. 3A and 3B are diagrams that schematically illustrate the process of registering an electro-anatomical map 56 with a three-dimensional (3-D) image 58 of the left atrium and associated blood vessels, in accordance with an embodiment of the present invention. Image 58 comprises a segmented pre-acquired image of the left atrium and pulmonary veins produced by a CT scanner.

FIG. 3A shows the map and 3-D image before the registration process. As can be seen in the figure, the map and 3-D image are not registered to a common coordinate system and generally have translation, rotation and scaling offsets with respect to one another.

Map 56 comprises an electro-anatomical map obtained using a catheter and a magnetic position tracking system, as described above. The map comprises a plurality of map points 60, each map point having a local activation value (expressed in milliseconds) in relation to a reference annotation, and a respective map coordinate. The different local activation values are shown in the figure using different shading patterns. Sites in which the physician already performed radio frequency (RF) ablation are marked with round circles.

The 3-D image comprises a plurality of image points 62, each having a respective image coordinate. Four anatomical landmarks denoted LAA, MPV, LIPV and MVA are identified both in map 56 and in 3-D image 58. The four landmarks respectively indicate the locations of the left atrial appendage, the medial pulmonary vein, the left inferior pulmonary vein and the mitral valve annulus. Note that all landmarks reside outside the target organ, i.e., outside the left atrium.

FIG. 3B shows map 56 and 3-D image 58 after the registration process is performed, in accordance with the method of FIG. 4 below. As can be seen in the figure, the map and 3-D image are now registered with a common coordinate system and displayed together.

Registration Method Description

Figure 4:
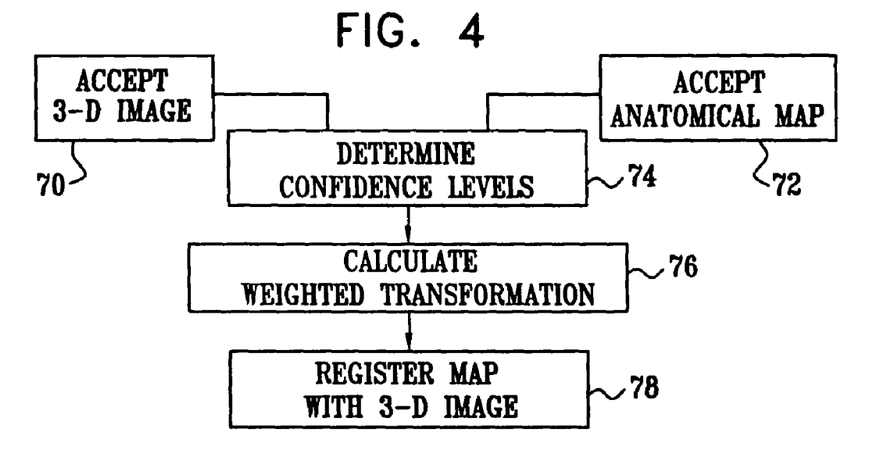
FIG. 4 is a flow chart that schematically illustrates a method for registering an electro-anatomical map with a pre-acquired 3-D image, in accordance with an embodiment of the present invention.

FIG. 4 is a flow chart that schematically illustrates a method for registering an electro-anatomical map with a pre-acquired 3-D image, in accordance with an embodiment of the present invention. The method of FIG. 4, carried out by display processor 42, takes into account varying confidence levels in the parameter map and/or 3-D image by assigning different weights to different map and image points when evaluating and minimizing a weighted cumulative distance metric.

The method begins with processor 42 accepting a pre-acquired 3-D image of the organ, at an image acceptance step 70. The 3-D image is represented by a plurality of image points 62 and associated coordinates. As noted above, at least part of the image points may in some cases define a 3-D solid, surface or wire-frame model of the imaged organ or parts thereof. Processor 42 further accepts an electro-anatomical map of the organ, at a map acceptance step 72. In some embodiments, the map is produced by magnetic position tracking system 20, as described above. The map is represented by a plurality of map points 60 and associated coordinates. The 3-D image and parameter map are accepted using interface 45 and provided to registration processor 46.

For at least some of the map points and/or image points, registration processor 46 determines confidence levels of the corresponding map and/or image coordinates, at a confidence assignment step 74. In some embodiments, some or all of the confidence levels are indicated to processor 46 by the physician or by another user. For example, the physician may review the map and/or 3-D image displayed on display 44 and mark areas or points of low or high confidence level using input device 47.

Additionally or alternatively, some or all of the confidence levels related to the map can be automatically determined by the system that produced the map (e.g., the position tracking system) during or after performing the location measurements, and provided to processor 46 along with the electro-anatomical map. Further additionally or alternatively, some or all of the confidence levels can be calculated automatically by processor 46 using the map and/or 3-D image, based on different criteria, such as the criteria described above.

Processor 46 calculates a geometrical transformation that best fits the map with the 3-D image, at a transformation calculation step 76. As described above, each map point is associated with a respective image point, and a distance is defined between the two points based on their coordinates. In order to reduce the effect of map and/or image points having low confidence levels and increase the effect of map and/or image points having high confidence levels, processor 46 assigns weights to the distances, based on the confidence levels. Processor 46 evaluates a weighted cumulative distance metric, such as the metric given in equation [2] above.

Processor 46 determines a geometrical transformation that minimizes the weighted cumulative distance metric, thus best fitting the map with the 3-D image, at a registration step 78. The resulting geometrical transformation typically comprises a combination of translation, rotation and/or scaling operations applied to either the map coordinates, the image coordinates, or to both. The registered map and 3-D image are then displayed to the physician using display 44, such as shown in FIG. 3B above.

Although the embodiments described herein refer mainly to a cardiac imaging system that uses a catheter equipped with a potential-sensing electrode, the methods described herein can be used in conjunction with any other suitable system that produces maps comprising measured parameters associated with coordinates. The parameter may be measured either locally or remotely. For example, a catheter fitted with an ultrasonic sensor and a position sensor can be used to produce maps of physiological parameters such as tissue density. These parameter maps can be registered with pre-acquired 3-D images using the methods described hereinabove.

Additionally or alternatively, the sensor measuring the parameter can be fitted in any other suitable intrabody probe, such as an endoscope. Further additionally or alternatively, the measurement of the parameter may be performed using an external sensor, such as an external ultrasonic transducer. The methods described herein can be used to process images and parameter maps of any other suitable organ, tissue or parts thereof, such as the aorta (AAA), coronaries, spine, neurological or any other cavity in which minimal invasive procedures are performed.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A computer-implemented method for image registration, comprising:

accepting on a computer a three-dimensional (3-D) image of an organ, the image comprising a first plurality of image points with respective image coordinates;

accepting on the computer a map defining a distribution of values of a physiological parameter over the organ, the map comprising a second plurality of map points with respective map coordinates, said second plurality of map points being sensed values of the physiological parameters;

associating respective confidence levels with one or more of the map coordinates and image coordinates;

assigning weights to at least some of the map points and image points responsively to the confidence levels of the respective map coordinates and image coordinates;

fitting the 3-D image with the map by calculating a geometrical transformation between the map coordinates and the image coordinates based on the weights; and displaying on the computer the fitted 3D image with the map.

2. The method according to claim 1, wherein accepting the map comprises measuring the values of the physiological parameter at the respective map coordinates using a position tracking system.

3. The method according to claim 2, wherein measuring the values and the map coordinates comprises moving a probe comprising a position sensor and a sensor measuring the physiological parameter over multiple locations in the organ, and performing respective multiple measurements of the physiological parameter and of a position of the position sensor at the locations.

4. The method according to claim 1, and comprising superimposing the values of the physiological parameter onto the 3-D image using the geometrical transformation, and displaying the superimposed values and 3-D image to a user.

5. The method according to claim 1, wherein fitting the 3-D image with the map comprises defining distances between at least some of the image points and respective map points, applying the weights assigned to the respective map points and image points to the distances to produce weighted distances, and calculating a cumulative weighted distance metric based on the distances, the metric indicative of an accuracy of the geometrical transformation in fitting the 3-D image with the map.

6. The method according to claim 5, wherein applying the weights comprises multiplying a square of the distances by the respective weights to produce the weighted distances, and wherein calculating the cumulative weighted distance metric comprises summing the weighted distances.

7. The method according to claim 5, wherein fitting the 3-D image with the map further comprises modifying the geometrical transformation so as to minimize the cumulative weighted distance metric.

8. The method according to claim 1, wherein fitting the 3-D image with the map comprises identifying an anatomical landmark external to the organ that appears in the 3-D image, acquiring a respective map point at a location of the anatomical landmark, and registering an image coordinate of the anatomical landmark in the 3-D image with a map coordinate of the acquired map point.

9. The method according to claim 1, wherein associating the confidence levels comprises accepting the confidence levels from a user.

10. The method according to claim 1, wherein associating the confidence levels comprises automatically determining the confidence levels based on the map points and image points.

11. The method according to claim 10, wherein automatically determining the confidence levels comprises detecting a distortion in at least one of the map coordinates and image coordinates and assigning the confidence levels responsively to a level of the distortion.

12. The method according to claim 10, wherein automatically determining the confidence levels comprises assigning the confidence levels responsively to at least one of:

a density of the respective one or more of the map coordinates in the map;

an electrical tissue characteristic in a vicinity of the respective map coordinates and image coordinates;

a physiological tissue characteristic in the vicinity of the respective map coordinates and image coordinates;

a distance of the respective map coordinates and image coordinates from a registration landmark identified in both the map and the 3-D image; and a physiological characteristic of the registration landmark.

13. The method according to claim 1, wherein accepting the 3-D image comprises accepting at least one of a solid model, a surface model and a wire-frame model of the organ defined by at least some of the image points.

14. Apparatus for image registration, comprising:

an interface, which is arranged to accept a three-dimensional (3-D) image of an organ, the image comprising a first plurality of image points with respective image coordinates, and to further accept a map defining a distribution of values of a physiological parameter over the organ, the map comprising a second plurality of map points with respective map coordinates, said second plurality of map points being sensed values of the physiological parameters; and a processor, which is arranged to associate respective confidence levels with one or more of the map coordinates and image coordinates, to assign weights to at least some of the map points and image points responsively to the confidence levels of the respective map coordinates and image coordinates, and to fit the 3-D image with the map by calculating a geometrical transformation between the map coordinates and the image coordinates based on the weights.

15. The apparatus according to claim 14, wherein the interface is arranged to accept the map from a position tracking system, which measures the values of the physiological parameter at the respective map coordinates.

16. The apparatus according to claim 14, wherein the position tracking system comprises a probe comprising a position sensor and a sensor measuring the physiological parameter, which is moved over multiple locations in the organ so as to perform respective multiple measurements of the physiological parameter and of a position of the position sensor at the locations.

17. The apparatus according to claim 14, wherein the processor is further arranged to superimpose the values of the physiological parameter onto the 3-D image using the geometrical transformation and to display the superimposed values and 3-D image to a user.

18. The apparatus according to claim 14, wherein the processor is arranged to define distances between at least some of the image points and respective map points, to apply the weights assigned to the respective map points and image points to the distances to produce weighted distances, and to calculate a cumulative weighted distance metric based on the distances, the metric indicative of an accuracy of the geometrical transformation in fitting the 3-D image with the map.

19. The apparatus according to claim 18, wherein the processor is arranged to multiply a square of the distances by the respective weights to produce the weighted distances, and to sum the weighted distances to produce the cumulative weighted distance metric.

20. The apparatus according to claim 18, wherein the processor is arranged to fit the 3-D image with the map by modifying the geometrical transformation so as to minimize the cumulative weighted distance metric.

21. The apparatus according to claim 14, wherein the processor is arranged to accept an identification of an anatomical landmark external to the organ that appears in the 3-D image and of a respective map point acquired at a location of the anatomical landmark, and to register an image coordinate of the anatomical landmark in the 3-D image with a map coordinate of the acquired map point.

22. The apparatus according to claim 14, wherein the processor is arranged to accept the confidence levels from a user via the interface.

23. The apparatus according to claim 14, wherein the processor is arranged to automatically determine the confidence levels based on the map points and image points.

24. The apparatus according to claim 14, wherein the processor is arranged to detect a distortion in at least one of the map points and image points and to assign the confidence levels responsively to a level of the distortion.

25. The apparatus according to claim 14, wherein the processor is arranged to assign the confidence levels responsively to at least one of:

a density of the respective one or more of the map coordinates in the map;

an electrical tissue characteristic in a vicinity of the respective map coordinates and image coordinates;

a physiological tissue characteristic in the vicinity of the respective map coordinates and image coordinates;

a distance of the respective map coordinates and image coordinates from a registration landmark identified in both the map and the 3-D image; and a physiological characteristic of the registration landmark.

26. The apparatus according to claim 14, wherein the 3-D image comprises at least one of a solid model, a surface model and a wire-frame model of the organ defined by at least some of the image points.

* * * * *